United States Patent

Meroni et al.

Patent Number: 6,156,885
Date of Patent: Dec. 5, 2000

[54] PROCESS FOR THE SYNTHESIS OF ALKYLPOLYGLUCOSIDES

[75] Inventors: Maria Luisa Meroni, Milan; Tullio Pellizzon, Paderno Dugnano, both of Italy

[73] Assignee: Condea Augusta S.p.A., Palermo, Italy

[21] Appl. No.: 09/181,916

[22] Filed: Oct. 29, 1998

[30] Foreign Application Priority Data

Oct. 30, 1997 [IT] Italy .................................. MI97A2437

[51] Int. Cl.⁷ .......................... C07H 15/00; C07H 17/00; C07G 3/00
[52] U.S. Cl. .......................... 536/18.6; 536/4.1; 536/18.5; 536/124
[58] Field of Search .................................... 536/4.1, 18.5, 536/18.6, 124

[56] References Cited

U.S. PATENT DOCUMENTS 3,547,828 12/1970 Mansfield et al. .
4,713,447 12/1987 Letton .
5,432,269 7/1995 Borsotti et al. .

FOREIGN PATENT DOCUMENTS 0 092 355 10/1983 European Pat. Off. .
0 132 043 1/1985 European Pat. Off. .
WO 90/07516 7/1990 WIPO .
WO 91/02742 3/1991 WIPO .

*Primary Examiner*—James O. Wilson
*Attorney, Agent, or Firm*—Oblon, Spivak, McClelland, Maier & Neustadt, P.C.

[57] ABSTRACT

The process for the synthesis of an alkylpolyglucoside having the formula (I):

$$H-(G)_n-O-R- \qquad (I)$$

wherein

R is linear or branched, saturated or unsaturated $C_8$–$C_{20}$ alkyl;

G is a radical resulting from removal of a molecule of water from a monosaccharide; and n is an integer from 1 to 5;

the process entailing reacting an alcohol with a monosaccharide or a compound capable of generating a monosaccharide in in situ, wherein the reaction is carried out in the presence of a catalyst consisting of one or more sterically hindered polyalkylarylsulfonic acids.

16 Claims, No Drawings

PROCESS FOR THE SYNTHESIS OF ALKYLPOLYGLUCOSIDES

BACKGROUND OF THE INVENTION

1. Field of the Invention

The present invention relates to an improved process for the synthesis of alkylpolyglucosides.

More specifically, the present invention relates to a process for the synthesis of alkylpolyglucosides characterized by the use of a sterically hindered polyalkylarylsulfonic acid or a mixture of sterically hindered polyalkylarylsulfonic acids as catalyst. Said catalyst allows a more selective reaction and consequently a reaction raw product which is practically without undesired by-products.

2. Discussion of the Background

Alkylpolyglucosides are a group of substances consisting of a chain of rings of a sugar linked to each other with glucosidic bonds in which the last ring of the glucosidic chain is acetalized with an alcohol. The general structure of alkylpolyglucosides is represented by the following general formula (I):

$$H\text{—}(G)_n\text{—}O\text{—}R \qquad (I)$$

wherein G represents a glucosidic unit, R represents the radical corresponding to the alcohol used for forming glucosidic acetal and n represents the polymerization degree, i.e. the number of glucosidic units linked.

Particularly important from an industrial point of view are alkylpolyglucosides in which n is between 1 and 5 and R represents the residue of a long-chain, aliphatic alcohol (linear or branched). The alkylpolyglucosides of this type, in fact, are non-ionic surface-active agents which can be used in the normal fields of use of surface-active agents and, in particular, in the field of detergents. These particular alkylglucosidic oligomers shall hereafter be indicated with the abbreviation APG. The control of the value of n can be effected by varying the molar ratio alcohol/saccharide in the preparation reaction of APG: by increasing this ratio, in fact, APG are obtained with a lower average value of n. Alternatively, it is possible to carry out a separation of the mixtures of APG obtained at the end of the productive cycle, operating as described in detail below.

APG offer, with respect to traditional surface-active agents, two important advantages: in the first place, they are obtained from renewable natural sources essentially consisting of starch and oil extracted from coconuts; secondly, APG are 100% biodegradable. As a result the industrial interest in these compounds is high and continually increasing.

The preparation of APG has been studied for many years and consequently various synthesis methods of these compounds are known starting from various combinations of reagents.

A first possibility is the direct synthesis starting from sugar and alcohol (or from a mixture of alcohols): the end product is obtained using the alcohol in excess with respect to the stoichiometric value. In an alternative synthesis method, the source of the glucosidic part of the molecule consists of starch obtained from cereals. In this case, the polysaccharide is generally first depolymerized with lower alcohols (methyl, or more commonly, butyl) in the presence of an acid as catalyst; in this way, a mixture of APG is obtained with a short-chain R group. This mixture is subsequently treated under vacuum with the long-chain alcohol, in the presence of an acid as catalyst, by the exchange of the alcohol group: this reaction is called "transacetalization" and is favoured by the removal, by evaporation, of the alcohol with a shorter chain which is formed and which is lower boiling than the long-chain alcohol; also in this case there is an excess of long-chain alcohol with respect to the stoichiometric value.

In both of the cases described above (direct synthesis of APG or by "transacetalization"), it is necessary to use an acid catalyst whose purpose is to favour the reactions which involve the glucosidic bond. The acids used for this purpose in industrial processes are mineral acids such as, for example, $H_2SO_4$, HCl, $H_3PO_4$ or $BF_3$, or, more commonly, sulfonic acids or their salts. The group of sulfonic acids used is very wide and comprises, for example, ortho-, meta- and paratoluenesulfonic acids, alkylbenzenesulfonic acids, secondary alkyl-sulfonic acids, sulfonic resins, alkylsulfates, alkylbenzenesulfonates, alkylsulfonates and sulfosuccinic acid. The use of these acids is described, for example, in patents DE 3.723.826, DE 3.842.541, DE 3.900.590, U.S. Pat. No. 4,950,743, EP 357.969, U.S. Pat. No. 4,223,129, U.S. Pat. No. 4,393,203, all relating to the use of paratoluenesulfonic acid (PTSA), which has been the most widely used for a long time; in European patent EP 449.866 which relates to the use of dinonyl naphthalenesulfonic acid; in U.S. Pat. No. 4,713,447 which relates to the use of dodecyl benzenesulfonic acid; in the patent DE 4.018.583 and in international patent application WO 91/02742 both relating to the use of sulfosuccinic acid; in U.S. Pat. No. 3,219,656 which relates to the use of sulfonic resins.

At the end of the reaction, the acid catalyst is neutralized with a base. The base which is most commonly used is sodium hydroxide (NaOH) but some patents claim the use of particular bases. For example, U.S. Pat. No. 4,713,447 describes the use of alcoholates of alkaline, earth-alkaline metals or of aluminum, or, alternatively, of salts of organic acids of the same metals.

The last passage in the synthesis process of APG consists in the separation of the APG themselves from the excess alcohol. This separation is generally carried out by distillation under vacuum, preferably thin film distillation, at a temperature of about 150° C.–180° C.; optionally, to facilitate this separation, it is possible to operate in the presence of fluidifying agents such as, for example, glycerine or glycols, or 1,2-diols with a long chain ($C_{12}$–$C_{18}$), as described, for example, in U.S. Pat. No. 4,889,925. Another technique used to separate the APG from the excess alcohol is the extraction with a solvent such as, for example, water, acetone or hypercritical $CO_2$. The selection of either of the separation techniques also allows the "cut" of the APG obtained, to be controlled: in fact, all the mixture of the APG obtained generally characterized by an average value of n within the range of 1.2–1.7, is recovered by distillation; whereas, by extraction with a solvent, the fractions with a lower molecular weight, substantially consisting of alkylmonoglucosides, remain in solution, and the fractions with a higher molecular weight, characterized by an average value of n higher than 1.7, generally between 1.7 and 2.5, are concentrated in the solid. This separation technique by extraction with a solvent is described, for example, in U.S. Pat. No. 3,547,828 and in European patent application EP 92.355.

A serious disadvantage, common to all the synthesis processes of APG known in the art, is the formation, as by-product, of polysaccharides: in fact, the monosaccharides most commonly used in the synthesis of APG are polyalcohols with five or six alchol groups which can compete with the long-chain alkyl alcohol in the formation of the glucosidic bond. In the most common case, i.e. operating with glucose or with one of its precursors, this secondary reaction causes the formation of polyglucose. This effect is undesired as, apart from substracting reagents from the main reaction, the polyglucose formed is a solid product whose presence in the mixture of products obtained, even in a small percentage, causes an increase in the viscosity of the mixture and the precipitation of products in a gelatinous form. As a result, all the subsequent operations of the synthesis process of APG, i.e. the separation of the desired product, the recovery and possible recycling of non-reacted alkylglucosides and alcohols, become extremely difficult.

To overcome this drawback, it is possible to operate with high alcohol/glucose ratios: this solution, however, involves the use of high volumes of alcohol, with consequent problems relating to the safety and overdimensioning of the APG production plants.

As a further possibility of limiting the formation of polyglucose, a proposal has been made to control the acid catalyst: it has been observed, in fact, that the type of catalyst used influences the composition of the raw reaction product. Operating, for example, as described in European patent EP 132.043, with a molar ratio alcohol/glucose of 2 to 1, in the presence of $H_2SO_4$ as catalyst, a percentage of polyglucose of more than 20% is obtained in the end-product after separation of the excess alcohol, whereas, in the presence of paratoluenesulfonic acid, this percentage is reduced to about 11%. Using alkaline alkylsulfonates or benzenesulfonic acids as catalysts, this percentage is further reduced to 9.2%. European patent EP 449.866 describes a new group of sulfonic acids showing a high lipophylia which, operating with a molar ratio alcohol/glucose of 5 to 1, enable the content of polyglucose to be lowered to 2.2% again calculated on the end-product after distillation of the excess alcohol; these catalyst, however, are very costly. In U.S. Pat. No. 5,432,269, using a binary catalyst consisting of the coupling of a weak base and a strong organic acid, operating with a ratio alcohol/glucose of 5 to 1, a percentage of polyglucose of 0.7% is obtained.

The Applicant has now found that a new group of catalysts consisting of a sterically hindered polyalkylarylsulfonic acid or a mixture of sterically hindered polyalkylarylsulfonic acids, allows the formation of polyglucose to be reduced in the synthesis process of APG, even when operating with low alcohol/glucose ratios.

The present invention therefore relates to a process for the synthesis of alkylpolyglucosides having general formula (I):

wherein:

R represents an alkyl radical, linear or branched, saturated or unsaturated, having a number of carbon atoms ranging from 8 to 20, extremes included;

G represents a radical resulting from the removal of a molecule of $H_2O$ from a monosaccharide, typically a hexose having the formula $C_6H_{12}O_6$ or a pentose having the formula $C_5H_{10}O_5$;

n is an integer between 1 and 5, extremes included;

said process comprising the reaction of an alcohol with a monosaccharide or an equivalent thereof, which can be an alkylglucoside or a compound capable of generating the nonosaccharide "in situ", characterized in that said reaction is carried out in the presence of a catalyst consisting of a sterically hindered polyalkylarylsulfonic acid or a mixture of sterically hindered polyalkylarylsulfonic acids.

Polyalkylarylsulfonic acids which can be used for the purposes of the present invention are those having at least one alkyl group, linear or branched, with a number of carbon atoms $\geq 10$, in ortho position with respect to the sulfonic group ($SO_3H$).

These polyalkylarylsulfonic acids are obtained by the sulfonation, using gaseous $SO_3$ in a film reactor, of heavy alkylates, linear or branched, present in the distillation residue coming from the synthesis of linear monoalkylbenzenes carried out starting from olefins and/or chloroparaffins in the presence of an excess of benzene and in the presence of a Friedel-Crafts catalyst: this synthesis is described, for example, in U.S. Pat. No. 5,574,198.

Preferred examples of polyalkylarylsulfonic acids, which can be used alone or mixed with each other, in the process of the present invention are those obtained by the sulfonation of ALCHISOR HD® of Condea Augusta S.p.A., which forms the distillation residue coming from the synthesis of linear alkylbenzene starting from benzene and olefins where these olefins are obtained by the dehydrogenation of n-paraffins. This residue contains:

polyalkylbenzenes ($\geq 80\%$ molar) having the general formula $C_nH_{2n-6}$ wherein n represents an integer between 16 and 45, extremes included;

dialkylbenzenes ($\geq 60\%$ molar) having the general formula $C_nH_{2n-6}$ wherein n represents an integer between 20 and 33, extremes included.

The polyalkylarylsulfonic acids described above can be defined by the following molecular formula:

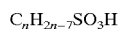

$$C_nH_{2n-7}SO_3H$$

wherein n represents an integer between 16 and 45, extremes included.

Or, these polyalkylarylsulfonic acids can be defined by the following general formula (II):

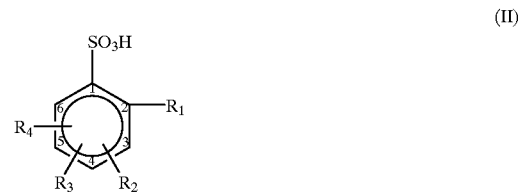

wherein:

$R_1$ represents a $C_{10}$–$C_{15}$ alkyl group, linear or branched, saturated or unsaturated;

$R_2$ represents a $C_1$–$C_{15}$ alkyl group, linear or branched, saturated or unsaturated, in ortho position (position 3 of the benzene ring) or meta position (position 4 or 6 of the benzene ring) or para position (position 5 of the benzene ring) with respect to the substituent $R_1$;

$R_3$ and $R_4$, the same or different, represent a hydrogen atom; or an alkyl group, linear or branched, saturated or unsaturated, having a number of carbon atoms which is such that the sum of the carbon atoms of the substituents $R_1$, $R_2$, $R_3$ and $R_4$, is equal to (n−6) wherein n represents an integer between 16 and 45, extremes included. For the purposes of the present invention, a mixture of dialkylbenzenesulfonic acids is preferably used, obtained by the sulfonation of ALCHISOR HD® which will hereinafter be indicated as DABS.

In the process of the present invention, the reaction between a monosaccharide or an equivalent thereof and an alcohol, is carried out at a temperature ranging from 110° C. to 130° C. under vacuum, with the continuous removal of the water which is formed.

Monosaccharides which can be conveniently used in the process of the present invention are, for example, glucose, mannose, galactose, arabinose, xylose, ribose, etc. Among these, glucose is preferred for its low cost and wide availability.

Corresponding to the above definition of equivalent compound of monosaccharide are alkylglucosides of lower alcohols such as, for example, butylglucosides; and higher sugars or saccharides which, under the reaction conditions, can be hydrolyzed to monosaccharides such as, for example, starch, maltose, sucrose, lactose, etc. Among the preferred precursors of monosaccharide, butylpolyglucosides obtained from the alcoholysis of starch or "corn syrup" can be mentioned as an example.

Alcohols which can be conveniently used in the process of the present invention are primary or secondary, monohydric alcohols, linear or branched, saturated or unsaturated, containing from 8 to 20 carbon atoms, and their mixtures.

Examples of the above alcohols are: octanol, decanol, lauryl alcohol, myristyl alcohol, oleyl alcohol, and alcohols deriving from oxosynthesis having a linear/branched ratio equal to 45/55 such as, for example, LIAL 111®, LIAL 123®, LIAL 145®, or their mixtures such as, for example, LIAL 125® (all sold by Condea Augusta S.p.A.), or fractions of linear alcohols obtained by fractionated crystallization of the above LIALs such as, for example, ALCHEM 111®, ALCHEM 123®, ALCHEM 145®, or their mixtures. It should be noted that the catalysts used in the process of the present invention make the use of fractions of $C_8$–$C_{20}$ totally branched alcohols such as, for example, ISALCHEM 123®, ISALCHEM 145®, or their mixtures (all sold by Condea Augusta S.p.A.), industrially convenient.

In the process of the present invention the alcohol is used in a higher quantity with respect to the stoichiometric value and, precisely, with a molar ratio between the alcohol and the monosaccharide ranging from 1 to 7, preferably between 1.5 and 3.3. The alcohol also acts as reaction solvent.

The catalyst can be used in a quantity ranging from 0.001 to 0.1 moles per mole of monosaccharide (or its equivalent) and, preferably, in a quantity ranging from 0.001 to 0.01 moles per mole of monosaccharide.

The reaction between the monosaccharide or its equivalent and the alcohol described above, can be carried out in batch or in continuous.

At the end of the reaction, the APG can be separated from the raw product by distillation or by treatment with a solvent in which the APG are almost totally insoluble.

The distillation is carried out according to methods known in the art (for example, distillation under vacuum).

In the case of treatment with a solvent such as, for example, acetone, two fractions are obtained; an insoluble fraction essentially consisting of APG having an average oligomerization degree >1.7, and a soluble fraction which remains in the solvent and essentially consists of APG having an average oligomerization degree generally between 1 and 1.2, the excess alcohol and practically all of the catalyst. The separation of the precipitate can take place by operating according to the methods known in the art such as, for example, by decanting or centrifugation.

The advantages of the use of the catalysts of the present invention are particulary evident in this phase. In fact, using the catalysts of the known art, after precipitation of the reaction mixture with the solvent, a gelatinous precipitate of APG is always obtained, with a high content of polysaccharides. As a result, all the separation and purification passages of the precipitate are lengthy and difficult. For example, using paratoluenesulfonic acid as catalyst, a gelatinous product is obtained whose washing by filtration on a porous septum requires times of about 10 hours and, in addition, owing to the gelatinous nature of the product, the washings are never complete and part of the alcohol and catalyst remain englobed in the product. With the catalysts used in the present invention, on the contrary, the content of polysaccharide is almost completely eliminated and, on addition of the solvent, a precipitate of APG is obtained whose washing by filtration on a porous septum requires only one hour and in which the other components of the raw reaction product do not remain englobed in the end-product, but are present only in traces.

This characteristic represents another important advantage of the process of the present invention: in fact, the washing liquid can be joined to the liquid phase obtained in the previous separation operation of the APG from the raw reaction product; this liquid phase, which contains excess alcohol, alkylmonosaccharides and practically all the catalyst, can be recycled to the reaction after evaporation of the solvent. Operating in this way, neutralization of the acid catalyst with bases which must be effected in many of the known processes in the art, is not necessary. The loss of catalyst, due to its englobement in the APG is extremely limited: operating in continuous, under optimum precipitation conditions and with the process in regime, there are losses of catalyst of about 0.5 g–1 g per 1 kg of end-product.

The above advantages are particularly evident when there are low alcohol/monosaccharide ratios; operating under these conditions is obviously desirable as it allows the volumes of alcohol necessary for the reaction, to be reduced, thus obtaining advantages in terms of cost, operational safety (alcohols in fact are flammable) and overall dimensions of the reactors used. In addition, as already mentioned above, a high alcohol/monosaccharide ratio leads to the synthesis of APG with a low average value of n, thus limiting the range of products to a fraction of those possible.

Also when distillation is carried out, the use of the catalysts of the present invention with respect to those of the known art, allows the production of APG in which the content of polysaccharide is almost completely eliminated.

The following illustrative examples are provided for a better understanding of the present invention and for its embodiment but do not limit its scope in any way.

EXAMPLE 1

800 g of LIAL 123® (4.12 moles, LIAL 123® is a mixture of linear and branched $C_{12}$–$C_{13}$ oxo-alcohols having an average molecular weight equal to 194) and 408 g of glucose monohydrate (2.06 moles) are charged into a 2-litre flask equipped with a stirrer, thermometer and distiller at the head; the molar ratio alcohol/glucose is 2.

The reaction mass is heated to 115° C. and subsequently, after removing the reaction water, 3.6 g (0.0078 moles) of DABS are introduced; the molar ratio catalyst/glucose is 0.0038.

The reaction flask is connected to a vacuum pump which maintains the internal pressure of the system at about 25 mm/Hg. The reaction proceeds, at a constant temperature (115° C.) and under vacuum, until the complete conversion of the glucose (about 6 hours); the reaction water which is formed is sent to a trap maintained at about –80° C.

The end-product which is obtained is a light viscous mass having a content of polyglucose, determined by high pressure liquid chromatography (HPLC), equal to 7%.

EXAMPLE 2

The reaction is carried out operating as described in Exmple 1, but using 6.9 g (0.015 moles) of DABS as catalyst; the molar ratio catalyst/glucose is 0.0073. The reaction time, determined from the complete conversion of the glucose, is about 5 hours.

The end-product obtained is a light viscous mass having a content of polyglucose, determined by high pressure liquid chromatography (HPLC), equal to 6%.

EXAMPLE 3

800 g of ALCHEM 123® (4.12 moles; ALCHEM 123® is a mixture of linear $C_{12}$–$C_3$ oxo-alcohols having an average molecular weight equal to 194) and 408 g of glucose monohydrate (2.06 moles) are charged into a 2-litre flask equipped with a stirrer, thermometer and distiller at the head; the molar ratio alcohol/glucose is 2.

The reaction mass is heated to 115° C. and subsequently, after removing the reaction water, 6.9 g (0.015 moles) of DABS are introduced; the molar ratio catalyst/glucose is 0.0073.

The reaction flask is connected to a vacuum pump which maintains the internal pressure of the system at about 25 mm/Hg. The reaction proceeds, at a constant temperature (115° C.) and under vacuum, until the complete conversion of the glucose (about 5 hours); the reaction water which is formed is sent to a trap maintained at about –80° C.

The end-product which is obtained is a light mass semi-solid at room temperature, having a content of polyglucose, determined by high pressure liquid chromatography (HPLC), equal to 5%.

EXAMPLE 4 (comparative)

The reaction is carried out operating as described in Example 1, but using 1.48 g of para-toluenesulfonic monohydrate acid as catalyst (0.0078 moles); the molar ratio catalyst/glucose is 0.0038. The reaction time, determined from the complete conversion of the glucose, is about 4 hours.

The end-product obtained is an amber-coloured, viscous mass having a content of polyglucose, determined by high pressure liquid chromatography (HPLC), equal to 15%.

EXAMPLE 5 (comparative)

The reaction is carried out operating as described in Example 2, but using 2.85 g of para-toluenesulfonic monohydrate acid as catalyst (0.015 moles); the molar ratio catalyst/glucose is 0.0073. The reaction time, determined from the complete conversion of the glucose, is about 3 hours.

The end-product obtained is an amber-coloured, viscous mass having a content of polyglucose, determined by high pressure liquid chromatography (HPLC), equal to 25%.

EXAMPLE 6 (comparative)

The reaction is carried out operating as described in Example 3, but using 1.48 g of para-toluenesulfonic monohydrate acid as catalyst (0.0078 moles); the molar ratio catalyst/glucose is 0.0073. The reaction time, determined from the complete conversion of the glucose, is about 3 hours.

The end-product obtained is a light gelatinous mass having a content of polyglucose, determined by high pressure liquid chromatography (HPLC), equal to 10%.

What is claimed is:

1. A process for the synthesis of an alkylpolyglucoside having the formula (I):

$$H-(G)_n-O-R-\qquad (I)$$

wherein:

R is linear or branched, saturated or unsaturated $C_8$–$C_{20}$ alkyl;

G is a radical resulting from removal of a molecule of water from a monosaccharide; and n is an integer from 1 to 5;

the process comprising reacting an alcohol with a monosaccharide or a compound which generates a monosaccharide in situ, said reaction being carried out in the presence of a catalyst consisting of one or more sterically hindered polyalkyarylsulfonic acids.

2. The process of claim 1, wherein the one or more polyalkylarylsulfonic acids have at least one linear or branched alkyl group, with a number of carbon atoms $\geq 10$, in an ortho position relative to the sulfonic acid group ($SO_3H$).

3. The process of claim 2, wherein the one or more polyalkylarylsulfonic acids have the following formula:

$$C_nH_{2n-7}SO_3H$$

wherein n is an integer from 16 to 45.

4. The process of claim 2, wherein the one or more polyalkylarylsulfonic acids have the formula (II):

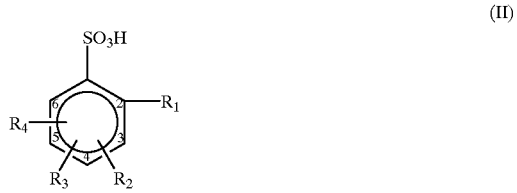

(II)

wherein:

$R_1$ is $C_{10}$–$C_{15}$ linear or branched, saturated or unsaturated alkyl;

$R_2$ is $C_1$–$C_{15}$ linear or branched, saturated or unsaturated alkyl, in an ortho position, or position 3 of the benzene ring, or meta position, or position 4 or 6 of the benzene ring, or para position, or position 5 of the benzene ring, with respect to the substituent $R_1$; and $R_3$ and $R_4$, are the same or different, and each represent hydrogen, linear or branched, saturated or unsaturated alkyl having a number of carbon atoms which is such that the sum of the carbon atoms of the substituents $R_1$, $R_2$, $R_3$ and $R_4$, is equal to (n–6) wherein n represents an integer from 16 to 45.

5. The process of claim 1, wherein the reaction between a monosaccharide or a precursor thereof and an alcohol is carried out at a temperature ranging from about 110° C. to 130° C. under vacuum, with continuous removal of water formed.

6. The process of claim 1, wherein the monosaccharides are selected from the group consisting of glucose, mannose, galactose, arabinose, xylose and ribose.

7. The process of claim 6, wherein the monosaccharide is glucose.

8. The process of claim 1, wherein the compound which generates a monosaccharide in situ is an alkylglucoside of a lower alcohol or a saccharide which, under reaction conditions, is hydrolyzed to a monosaccharide.

9. The process of claim 8, wherein said alkylglucoside of said lower alcohol is butyl glucoside.

10. The process of claim 8, wherein said saccharide which is hydrolyzed to said monosaccharide is starch, maltose, sucrose or lactose.

11. The process of claim 1, wherein the alcohol is a primary or secondary monohydric alcohol, which is linear or branched, saturated or unsaturated, and contains from 1 to 20 carbon atoms or a mixture thereof.

12. The process of claim 1, wherein the molar ratio between alcohol and monosaccharide is from 1 to 7.

13. The process of claim 12, wherein the molar ratio between alcohol and monosaccharide is between 1.5 and 3.3.

14. The process of claim 1, wherein the catalyst is used in a quantity ranging from 0.0001 to 0.01 moles per mole of monosaccharide or an equivalent thereof.

15. The process of claim 1, wherein the monosaccharide is pentose or hexose.

16. The process of claim 14, wherein the catalyst is used in a quantity ranging from 0.01 to 0.1 moles per mole of monosaccharide or said compound which generates a monosaccharide in situ.

* * * * *